(12) United States Patent
Horino et al.

(10) Patent No.: US 11,871,992 B2
(45) Date of Patent: Jan. 16, 2024

(54) SUBJECTIVE OPTOMETRY SYSTEM

(71) Applicant: NIDEK CO., LTD., Aichi (JP)

(72) Inventors: Taeko Horino, Aichi (JP); Hirohisa Terabe, Aichi (JP); Jouji Seko, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 17/484,762

(22) Filed: Sep. 24, 2021

(65) Prior Publication Data

US 2022/0095910 A1 Mar. 31, 2022

(30) Foreign Application Priority Data

Sep. 29, 2020 (JP) .................................. 2020-164149

(51) Int. Cl.
*A61B 3/036* (2006.01)
(52) U.S. Cl.
CPC ................................. *A61B 3/036* (2013.01)
(58) Field of Classification Search
CPC ..................................................... A61B 3/036
USPC .......................................................... 351/222
See application file for complete search history.

(56) References Cited

U.S. PATENT DOCUMENTS

2006/0287688 A1* 12/2006 Yonezawa .......... A61N 1/36046
607/54
2014/0118694 A1* 5/2014 Fujiu ........................ A61B 3/14
351/246
2015/0055088 A1* 2/2015 Shimizu .................... A61B 3/12
351/205
2015/0190047 A1* 7/2015 Sugiura ................ A61B 3/0033
351/233
2015/0342454 A1* 12/2015 Foster .................... A61B 3/032
351/246
2017/0135572 A1* 5/2017 Takii ........................ A61B 3/04
2018/0064339 A1* 3/2018 Takii .................... A61B 3/0091
2018/0078135 A1* 3/2018 Takii .................... A61B 3/0025
2019/0099073 A1* 4/2019 Takii ........................ A61B 3/08

FOREIGN PATENT DOCUMENTS

EP          3381350 A1 * 10/2018   .............. A61B 3/02
JP      2020018712 A      2/2020

* cited by examiner

*Primary Examiner* — William R Alexander
*Assistant Examiner* — Sharrief I Broome
(74) *Attorney, Agent, or Firm* — Sughrue Mion, PLLC (57) ABSTRACT

A subjective optometry system includes a plurality of subjective optometry devices and a database which stores at least any data of objective measurement data and previous glass data in association with each identifier. Each of the subjective optometry devices includes a calibration optical system, an information processor, and a reader which is connected to the information processor, reads an identifier prepared for each examinee, and outputs information about the read identifier to the information processor. The information processor acquires at least one of the objective measurement data and the previous glass data corresponding to the identifier from the database based on the identifier received from the reader, and sets an initial value of the calibration optical system used on an occasion of subjectively measuring optical characteristics of a subject eye based on at least one of the objective measurement data and the previous glass data.

11 Claims, 5 Drawing Sheets

| DATABASE SETTING | | |
|---|---|---|
| SELECT | SETTING TARGET DEVICE | NAME OF MEMBER |
| ○ | FIRST SUBJECTIVE OPTOMETRY DEVICE | MEMORY |
| | FIRST SUBJECTIVE OPTOMETRY DEVICE | RELAY UNIT |
| | SECOND SUBJECTIVE OPTOMETRY DEVICE | MEMORY |
| | CONTROL DEVICE | DEDICATED MEMORY |

SUBJECTIVE OPTOMETRY SYSTEM

CROSS-REFERENCE TO RELATED APPLICATION

This application claims priority from Japanese Patent Application No. 2020-164149 filed on Sep. 29, 2020, the entire subject-matter of which is incorporated herein by reference.

TECHNICAL FIELD

The present disclosure relates to a subjective optometry system used for subjectively measuring optical characteristics of a subject eye.

BACKGROUND

A subjective optometry device that measures optical characteristics such as an eye refractive power of a subject eye by arranging optical elements in front of an eye of an examinee and presenting an examination target to the subject eye through the optical elements, is known. For example, a subjective optometry device disclosed in JP-A-2020-18712 includes an eye refractive power measurement apparatus, a target presentation device, and a controller. The eye refractive power measurement apparatus switches the optical elements to be arranged in an optometry window among a plurality of optical elements provided by the calibration optical system using a driver. The target presentation device switches the examination target presented to the subject eye. The controller detects a user's operation on an operation panel and transmits a drive signal to the eye refractive power measurement apparatus and the target presentation device based on the detected operation.

In addition, when starting the measurement using the subjective optometry device described above, in order to perform the initial setting on the subjective optometry device, objective measurement data measured by the objective measurement device and previous glass data of glasses worn by the examinee measured by a lens meter are taken into the subjective optometry device, and then, an examination efficiency is improved. The objective measurement data and previous glass data described above are managed for each examinee.

Incidentally, it is desired to provide a mechanism that can efficiently examine the examinee by arranging a plurality of subjective optometry devices at various places and enabling the operation of each subjective optometry device from various places. Therefore, an inventor studied a subjective optometry system that makes the examination can be performed by operating each subjective optometry device using each information processor from various places.

With regard to such a subjective optometry system, when each subjective optometry device takes the objective measurement data, the previous glass data, and the like and starts the subjective measurement, since a plurality of subjective optometry devices are connected, it becomes difficult to grasp an information processor of the subjective optometry device that requires the objective measurement data, the previous glass data, and the like, and thus, it turned out that it is difficult to grasp the subjective optometry device on which the initial setting should be executed.

SUMMARY

A technical object of the present disclosure is to provide a subjective optometry system that can easily perform initial settings in each subjective optometry device in a subjective optometry system including a plurality of subjective optometry devices.

A subjective optometry system including:
a plurality of subjective optometry devices, which are used to subjectively measure optical characteristics of a subject eye, each including:
 a calibration optical system that changes optical characteristics of a target light flux presented to the subject eye;
 an information processor for operating the subjective optometry device; and
 a reader that is connected to the information processor, reads an identifier prepared for each examinee, and outputs information about the read identifier to the information processor; and
a database that stores at least any data of objective measurement data and previous glass data in association with each identifier,
in which the information processor is configured to:
 acquire at least one of the objective measurement data and the previous glass data corresponding to the identifier from the database, based on the identifier received from the reader; and
 set an initial value of the calibration optical system used on an occasion of subjectively measuring optical characteristics of the subject eye, based on at least one of the objective measurement data and the previous glass data.

A subjective optometry system including:
a subjective optometry device, which is used to subjectively measure optical characteristics of a subject eye, including:
 a calibration optical system that changes optical characteristics of a target light flux presented to the subject eye;
 an information processor for operating the subjective optometry device; and
 a reader that is connected to the information processor, reads an identifier prepared for each examinee, and outputs information about the read identifier to the information processor;
a database that stores at least any data of objective measurement data and previous glass data in association with each identifier; and
a remote information processor that is connected to the information processor, and remote-accesses the information processor to operate the subjective optometry device via the information processor,
in which the information processor is configured to:
 acquire at least one of the objective measurement data and the previous glass data corresponding to the identifier from the database, based on the identifier received from the reader; and
 output acquired data being at least one of the objective measurement data and the previous glass data to the remote information processor to notify the remote information processor of at least one of the objective measurement data and the previous glass data.

DETAILED DESCRIPTION

Overview

Hereinafter, a typical embodiment will be described with reference to the drawings. FIG. 1 to FIG. 4 are diagrams for explaining the subjective optometry system relating to the present embodiment. The items classified by < and > below can be used independently or in relation to each other.

A subjective optometry system (for example, a subjective optometry system 100) in the present embodiment includes a plurality of subjective optometry devices (for example, a first subjective optometry device 1, a second subjective optometry device 1A, and a third subjective optometry device 1B). In addition, for example, the subjective optometry system includes a database (for example, a database 72).

For example, the plurality of subjective optometry devices are used for subjectively measuring optical characteristics of a subject eye. For example, the optical characteristics of the subject eye that are subjectively measured may be at least one of an eye refractive power (for example, a spherical power, an astigmatic power, an astigmatic axis angle, and the like), a contrast sensitivity, and a binocular visual function (for example, an oblique amount, a stereoscopic visual function, and the like).

For example, each subjective optometry device in a plurality of subjective optometry devices has a calibration optical system (a calibration optical system 11), an information processor (for example, an information processor 20), and a reader (for example, a reader 30), respectively. For example, the calibration optical system changes the optical characteristics of a target light flux presented to the subject eye. For example, the information processor is used for operating the subjective optometry device. For example, the reader is connected to the information processor, reads an identifier prepared for each examinee, and outputs the information about the read identifier to the information processor. For example, the connection between the reader and the information processor may be a direct connection or may be a connection via another member.

For example, the connections between various devices are the connections via a network. For example, as the network, at least one of wireless and wired configurations may be used. For example, the subjective optometry system performs communications between various devices using at least one of the wireless and the wired configurations. For example, the wireless configuration may be a wireless LAN, an infrared communication, Wi-Fi (registered trademark), Bluetooth (registered trademark), or the like. In addition, the wired configuration may be a USB cable, a LAN cable, or the like.

For example, regarding each of the calibration optical system, the information processor, and the reader included in the subjective optometry device, between each of the subjective optometry devices, the configuration of at least any one of the calibration optical system, the information processor, and the reader may be partially different from the configuration of another subjective optometry device, or may be the same configuration as the configuration of another subjective optometry device.

For example, at least any data of the objective measurement data and the previous glass data is stored in the database in association with each identifier. For example, the identifier can be selected as appropriate. For example, at least one of a QR code (registered trademark), a barcode, an identification hole formed by a predetermined rule, a list of characters and patterns, and the like can be adopted as the identifier. Of course, an identifier different from the above may be used. In this case, for example, the reader may be an identifier reader (for example, a QR code (registered trademark) reader, a barcode reader, an identification hole reader, and the like) corresponding to the identifier used.

For example, in the present embodiment, the information processor acquires at least one of the objective measurement data and the previous glass data corresponding to the identifier from the database based on the identifier received from the reader. In addition, for example, the information processor sets the initial value of the calibration optical system used on an occasion of subjectively measuring the optical characteristics of the subject eye, based on at least one of the objective measurement data and the previous glass data.

For example, the optical characteristics set as the initial value may include at least one of a spherical power, a cylindrical power, a cylindrical axis, polarization characteristics, an aberration amount, and the like. Of course, optical characteristics other than the above may be set as the initial value. For example, the optical characteristics set as the initial value may be a pupillary distance (PD).

For example, the objective measurement data may be data obtained by objectively measuring the optical characteristics of the subject eye. For example, the optical characteristics of the subject eye that are objectively measured includes the eye refractive power (for example, the spherical power, the astigmatic power, the astigmatic axis angle, and the like), the polarization characteristics, the pupillary distance, and the like.

For example, the previous glass data may be the data obtained by measuring the optical characteristics of the glasses worn by the examinee. For example, the optical characteristics of the glasses include the refractive power (for example, the spherical power, the astigmatic power, the astigmatic axis angle, and the like), the polarization characteristics, the pupillary distance, and the like.

For example, when only one of the objective measurement data and the previous glass data is acquired as the data corresponding to the identifier, the initial value may be set based on the acquired data.

In addition, for example, when both the objective measurement data and the previous glass data are acquired as the data corresponding to the identifier, any one of those data may be selected. In this case, for example, a selection screen for selecting which of the data will be based on for setting the initial value may be displayed on a display unit (for example, a display unit 24) of the information processor. Of course, the selection may be performed by different methods. In addition, for example, the data to be prioritized is set in advance and when both the objective measurement data and the previous glass data are acquired, the initial value may be set based on the data set in advance.

In addition, for example, when both the objective measurement data and the previous glass data are acquired as the data corresponding to the identifier, the initial value may be set based on both. In this case, for example, the initial value may be set based on average value data of the objective measurement data and the previous glass data. Of course, the configuration for setting the initial value using both data is not limited to the above.

As described above, for example, the subjective optometry system in the present embodiment includes a plurality of subjective optometry devices which are used to subjectively measure the optical characteristics of the subject eye, and a database in which at least any data of the objective measurement data and the previous glass data is stored in association with each identifier. Each of the subjective optometry devices includes a calibration optical system which changes the optical characteristics of the target light flux presented to the subject eye, an information processor for operating the subjective optometry device, and a reader which is connected to the information processor, reads the identifier prepared for each examinee, and outputs the information about the read identifier to the information. In addition, for example, the information processor acquires at least one of the objective measurement data and the previous glass data corresponding to the identifier from the database based on the identifier received from the reader, and sets the initial value of the calibration optical system used on an occasion of subjectively measuring the optical characteristics of the subject eye based on at least one of the objective measurement data and the previous glass data.

As described above, for example, by connecting the reader to the information processor of each subjective optometry device, the identifier information read by the reader is output to the connected information processor, since the information processor that received the identifier information acquires the data corresponding to the identifier, it is possible to easily grasp the information processor of the subjective optometry device that requires the data corresponding to the identifier. In other words, by connecting the subjective optometry system to the database via the information processor connected to the reader that reads the identifier, it is possible to easily grasp the information processor of the subjective optometry device that requires the data corresponding to the identifier. Therefore, in the subjective optometry system in which a plurality of subjective optometry devices can be connected to the database, when at least any data of the objective measurement data and the previous glass data is acquired from the database, it is possible to suppress a problem of not knowing the information processor of the subjective optometry device that requires the data. That is, even in a subjective optometry system in which the information processor of a plurality of subjective optometry devices can be connected, in the processing for the identifier read by the reader, it is possible to easily grasp the subjective optometry device on which the initial setting (setting the initial value) should be executed.

In addition, for example, by collectively managing the information on the examinee in association with the identifier, various data can be easily acquired based on the identifier, and thus, it is possible to easily set the initial value of the calibration optical system used on an occasion of subjectively measuring the optical characteristics of the subject eye. Therefore, erroneous input of examinee information and an effort of the examiner to input the data can be suppressed, and thus, it is possible to accurately and smoothly start the subjective measurement in each subjective optometry device.

<Past Subjective Measurement Data>

In the description above, a configuration using at least any data of the objective measurement data and the previous glass data as the data corresponding to the identifier has been described as an example, but the present disclosure is not limited to this. Furthermore, the subjective measurement data which is a past subjective measurement result of the examinee performing the subjective measurement may be used as the data.

In this case, for example, subjective measurement data measured on different days (measured in the past) may be stored in the database in association with each identifier. For example, the information processor may acquire the subjective measurement data corresponding to the identifier from the database based on the identifier received from the reader, and the initial value of the calibration optical system used on an occasion of subjectively measuring the optical characteristics of the subject eye may be set based on the subjective measurement data. With such a configuration, for example, the subjective measurement data can be used instead of the previous glass data and the objective measurement data, it is possible to set the initial value smoothly.

In the description above, in addition to at least any data of the objective measurement data and the previous glass data, the subjective measurement data can be used as the data corresponding to the identifier as an example, but the present disclosure is not limited to this. At least any of the objective measurement data, the previous glass data, and the subjective measurement data may be used as the data corresponding to the identifier. In this case, for example, at least any data of the objective measurement data, the previous glass data, and the subjective measurement data may be stored in the database in association with each identifier. For example, the information processor may acquire at least one of the objective measurement data, the previous glass data, and the subjective measurement data corresponding to the identifier from the database based on the identifier received from the reader, and may set the initial value of the calibration optical system used on an occasion of subjectively measuring the optical characteristics of the subject eye based on at least one of the objective measurement data, the previous glass data, and the subjective measurement data.

For example, the subjective measurement data may be the data obtained by subjectively measuring the optical characteristics of the subject eye. For example, the eye refractive power (for example, the spherical power, the astigmatic power, the astigmatic axis angle, and the like), the polarization characteristics, and the like can be exemplified as the optical characteristics of the subject eye measured subjectively. In acquiring the subjective measurement data, the subjective measurement data may be acquired by the same device as the subjective optometry device that performs the subjective measurement or the subjective measurement data may be acquired by different devices.

<Initial Value Setting>

For example, the information processor may automatically set the initial value based on the identifier received from the reader. In addition, for example, the information processor may be configured to set the initial value via the operation of the examiner or the examinee based on the identifier received from the reader.

For example, a case of automatically setting the initial value will be described. For example, when receiving the identifier information, the information processor may automatically acquire at least one of the objective measurement data and the previous glass data corresponding to the identifier from the database, and may automatically set the initial value of the calibration optical system based on at least one of the objective measurement data and the previous glass data. With such a configuration, for example, when the reader reads the identifier, since the acquisition of the data can be performed quickly and the initial value can be set, it is possible to easily set to start the subjective measurement without operating the information processor by the examinee or examiner. In particular, when the examinee uses the information processor to perform the examination by himself (self-examination), since it is difficult to understand the state of the information processor and the operation method, this technology is useful.

For example, the case where the information processor sets the initial value via the operation of the examiner or the examinee based on the identifier received from the reader will be described. For example, when receiving the identifier information, the information processor may check the examiner or the examinee whether or not to acquire at least one of the objective measurement data and the previous glass data corresponding to the identifier, from the database. In this case, for example, the information processor may display a confirmation screen as to whether or not to acquire the data on a display screen of the information processor so as to allow the examiner or the examinee to select whether or not to acquire the data. In addition, for example, after acquiring at least one of the objective measurement data and the previous glass data corresponding to the identifier from the database, the information processor may check the examiner or the examinee whether or not to set the initial value of the calibration optical system. In this case, for example, the information processor may display a confirmation screen as to whether or not the examiner or the examinee sets the initial value of the calibration optical system based on the acquired data on the display unit of the information processor so as to allow the examiner or the examinee to select whether or not to acquire the data. With such configurations, it is possible to smoothly execute the initial setting when causing the examiner or the examinee to start the subjective measurement. In addition, even if the examiner or the examinee erroneously reads a different identifier, it is possible to easily perform the calibration. In addition, since the examiner or the examinee can determine whether or not to set the initial value, if there is a feeling of discomfort in the acquired data, it is possible to take appropriate measures according to the situation.

<Storage in Database>

For example, the subjective optometry system may include a setting device (for example, the controller 71) for recording the data in the database in association with the identifier. In this case, for example, the subjective optometry system may include a data acquisition device (for example, the controller 71) and a database setting device. For example, the data acquisition device may acquire at least any data of the objective measurement data and the previous glass data. In addition, for example, the database setting device may record at least any data of the objective measurement data and the previous glass data acquired by the data acquisition device, in the database, in association with the identifier. With such a configuration, for example, for each examinee, the identifier and the data are stored in the database in a state of being appropriately associated with each other. Therefore, by reading the identifier, appropriate data is acquired for each examinee.

For example, when acquiring at least any data of the objective measurement data and the previous glass data, the data acquisition device may acquire at least any data of the objective measurement data and the previous glass data by receiving the data input to the subjective optometry system by the input from the operator. In addition, for example, when acquiring at least any data of the objective measurement data and the previous glass data, the data acquisition device may acquire at least any data of the objective measurement data and the previous glass data by receiving the data measured by a device different from the subjective optometry device (for example, an objective measurement device or a lens meter). In addition, for example, when acquiring at least any data of the objective measurement data and the previous glass data, the subjective optometry device may include measurement means for measuring at least any data of the objective measurement data and the previous glass data the measurement is performed by the measurement means, and then, the data acquisition device may acquire at least any data of the objective measurement data and the previous glass data.

<Database Setting>

For example, the database can be set in any configuration. For example, any memory (for example, the memory 22) among the memories included in the subjective optometry devices may be used as the database. In addition, for example, a dedicated memory (for example, the database 72) dedicated to the database may be used as the database.

For example, a case where the memory of the subjective optometry device is used as the database will be described. For example, each of plurality of subjective optometry device may include the memory, and the database may be set in the memory of any of the plurality of subjective optometry devices. In this case, for example, the memory used as the database is set from the memory of each of the plurality of subjective optometry devices. For example, another subjective optometry device (for example, the information processor) is connected to the memory used as the database, and a subjective optometry system is constructed. According to such a configuration, for example, a subjective optometry system can be constructed with a simple configuration without requiring a separate dedicated configuration for providing a database.

In addition, for example, a case where the dedicated memory dedicated to the database is used as the database will be described. For example, the database may be set in a dedicated memory that is different from the memory of the subjective optometry device and is provided in a dedicated manner for setting the database. In this case, for example, each subjective optometry device (for example, the information processor) is connected to the dedicated memory used as the database, and the subjective optometry system is constructed. According to such a configuration, it is possible to smoothly acquire the data without imposing a load on the memory of the predetermined subjective optometry device. As the dedicated memory, the memory included in a personal computer (hereinafter, referred to as a "PC") provided for the database may be used. Of course, the dedicated memory is not limited to the memory in the PC. For example, the memory in a server, a mobile terminal, or a smartphone may be used. Of course, the memory (storage unit) having only a storage function may be used.

For example, the memory of the subjective optometry device, the dedicated memory dedicated to the database, and the memory used as the database may be switched. For example, each of a plurality of subjective optometry devices has the memory. In addition, for example, a selection unit (for example, a controller 71) that can selectively set a memory used as the database among a dedicated memory different from the memory and is provided in a dedicated manner for setting the database and the memories of the subjective optometry devices, may be provided.

In this case, for example, the memory in which the database is set may be selectively set by a constructor who constructs the subjective optometry system. That is, the constructor selects the memory to be used as the database by using an operation unit (for example, the operation unit 73)

for setting. As an example of a configuration for performing the selection, for example, the memory that can be used as the database may be displayed on the display screen of the operation unit, the constructor may operate the operation unit to select the memory to be used as the database from the memory displayed on the display screen of the operation unit. For example, the selection unit may set a memory selected by the operation unit as the database. Of course, the memory may be automatically selected by the controller of the operation unit for performing the setting. For example, at least one of a PC, a mobile terminal, a smartphone, and the like may be used as the operation unit. Of course, the other operation unit different from the above may be used.

As described above, for example, when setting the database, depending on the location where the plurality of subjective optometry devices are installed, the configuration for setting the database can be changed, and it is possible to construct the appropriate subjective optometry system according to the purpose of the examiner. As an example, in a case of a subjective optometry system in which a plurality of subjective optometry devices are arranged in a common building (for example, a store, a hospital, and the like) (for example, cooperation in a common building), by setting the database in the memory of the subjective optometry device, it is possible to construct the subjective optometry system with a simple configuration without requiring a separate configuration for providing a database. In addition, as an example, in a case of a subjective optometry system in which a plurality of subjective optometry devices are arranged in different buildings (for example, distant stores, distant hospitals, and the like) (for example, cooperation outside the common building), by setting the database in the dedicated memory provided for the database in a dedicated manner, it is possible to smoothly acquire the data without imposing a load on the memory of the predetermined subjective optometry device.

In the description above, for example, when the memory of the subjective optometry device is used as the database, a relay unit (for example, the relay unit 19) of the subjective optometry device may be used as the memory. In this case, for example, a relay unit may be provided, which is connected to the subjective optometry device and the information processor, relays an operation signal from the information processor to the subjective optometry device, and allows the subjective optometry device to be operated based on the operation signal. In addition, for example, the relay unit may also serve as the memory. As described above, for example, by the relay unit also serving as the memory, even if various types of information processors that are different for each subjective optometry device are used, it is possible to easily perform the acquisition of the data corresponding to the identifier.

For example, the relay unit may be configured to be able to relay such that each member of the subjective optometry device can be operated by the operation signal from the information processor. For example, the relay unit may be configured to convert the operation signal from the information processor into the drive signal which drives the subjective optometry device such that the subjective optometry device can be operated by the operation signal from the information processor. That is, the relay unit may be configured to convert the operation signal from the information processor into a drive signal that can drive the subjective optometry device according to the various subjective optometry devices. Of course, for example, the relay unit may be configured to relay only the operation signal. With such a configuration, for example, even when various subjective optometry devices are used, since the communication corresponding to the subjective optometry device can be performed, and thus, it is possible to appropriately operate the subjective optometry device. In addition, for example, even when various information processors are used, since the communication corresponding to the information processor can be performed, it is possible to appropriately operate the subjective optometry device.

Remote Information Processor

For example, the subjective optometry system may include a remote information processor (for example, the remote information processor 80) capable of operating the subjective optometry device from a remote access destination. In this case, for example, the subjective optometry system may include a remote information processor that is the remote information processor connected to the information processor, and is a remote information processor for operating at least any one of the subjective optometry devices of a plurality of subjective optometry devices via the information processor by remote-accessing the information processor. In addition, for example, by outputting at least one of the acquired objective measurement data and the previous glass data to the remote information processor, the information processor may notify the remote information processor of at least one of the objective measurement data and the previous glass data.

With such a configuration, for example, it is possible to provide the data to the remote information processor that remote-accesses the information processor of the subjective optometry device that requires the data corresponding to the identifier. In this way, even when operating the subjective optometry device from the remote access destination (for example, a remote location or the like), the examiner can confirm the examinee data, and thus, it is possible to set an appropriate initial value of the subjective optometry device on which the initial setting should be performed.

For example, the remote information processor receives at least one of the objective measurement data and the previous glass data output from the information processor. For example, the remote information processor may output the received data such that examiner can confirm. In this case, for example, the remote information processor may include an output unit (for example, the controller 81). For example, the output unit may display the data on a display unit (for example, the display unit 84) of the remote information processor. In addition, for example, the output unit may be configured to print the data.

For example, the instructions for setting the initial value may be given by the remote information processor or may be given by the information processor. For example, if the remote information processor gives the instructions for setting the initial value, the remote information processor may output an instruction signal for setting the initial value of the calibration optical system used on an occasion of subjectively measuring the optical characteristics of the subject eye. For example, the information processor may set the initial value of the calibration optical system which is based on at least one of the objective measurement data and the previous glass data, according to the instruction signal from the remote information processor. For example, the setting of the initial value based on the instruction may be performed by the information processor or may be performed by the remote information processor.

For example, when the information processor gives the instructions for setting the initial value, the examiner who confirmed the data by the remote information processor may communicate with the examiner or examinee operating the information processor using a communication tool (for example, a microphone, a speaker, or the like). For example, the examiner or examinee operating the information processor may operate the information processor and give the instructions for setting the initial value by referring to the communication from the examiner operating the remote information processor.

For the output of the instruction signal regarding the initial value, the configuration described in the information processor in the above <initial value setting> can be applied. As an example, by displaying the confirmation screen of the information processor in <initial value setting> on the remote information processor, and by operating the remote information processor the examiner or examinee, the output of the instruction signal may be performed.

In the description above, a configuration using at least any data of the objective measurement data and the previous glass data as the data corresponding to the identifier has been described as an example, but the present disclosure is not limited to this. Furthermore, the subjective measurement data which is a past subjective measurement result of the examinee performing the subjective measurement may be used as the data. In this case, for example, by the information processor outputting at least one of the acquired objective measurement data, the previous glass data, and the subjective measurement data to the remote information processor, for example, the subjective optometry system may notify of at least one of the objective measurement data, the previous glass data, and the subjective measurement data to the remote information processor.

In the configuration described above, as the subjective optometry system in a case of using the remote information processor, the configuration having a plurality of subjective optometry devices is described as an example, but the present disclosure is not limited to this. As the subjective optometry system in a case of using the remote information processor may be a case of having at least one or more subjective optometry devices.

In this case, for example, the subjective optometry system may include the subjective optometry device including the calibration optical system that changes the optical characteristics of the target light flux presented to the subject eye, the Information processor for operating subjective optometry device, and the reader that is connected to the information processor, reads the identifier prepared for each examinee, and outputs the information about the read identifier to the information processor, and is used for subjectively measuring the optical characteristics of the subject eye, and the database in which at least any data of the objective measurement data and the previous glass data are stored in association with each identifier, and the remote information processor connected to the information processor, and is a remote information processor for operating the subjective optometry device via the information processor by remote-accessing the information processor. In addition, for example, the information processor may acquire at least one of the objective measurement data and the previous glass data corresponding to the identifier from the database based on the identifier received from the reader, and may notify the remote information processor of at least one of the objective measurement data and the previous glass data by outputting at least one of the acquired objective measurement data and the previous glass data to the remote information processor. With such a configuration, for example, even when operating the subjective optometry device from a remote access destination (for example, the remote location), the examiner can confirm the data of the examinee, and it is possible to set the appropriate initial value of the subjective optometry device.

For example, the remote information processor may output the instruction signal for setting the initial value of the calibration optical system used on an occasion of subjectively measuring the optical characteristics of the subject eye, and the information processor may set the initial value of the calibration optical system which that is based on at least one of the objective measurement data and the previous glass data, according to the instruction signal from the remote information processor.

<Calibration Optical System>

For example, any configuration may be used as long as the calibration optical system is configured to change the optical characteristics (for example, at least any one of the spherical power, the astigmatic power, the astigmatic axis angle, the polarization characteristics, the aberration amount, and the like) of the target light flux presented to the subject eye. For example, as the configuration for changing the optical characteristics of the target light flux, the optical elements may be controlled. For example, as the optical elements, at least any one of a spherical lens, a cylindrical lens, a cross cylinder lens, a rotary prism, a wave surface modulation element, and the like may be used. Of course, for example, as the optical elements, optical elements different from the above-described optical elements may be used.

For example, the calibration optical system may have a configuration in which the spherical power of the subject eye is corrected by optically changing a presentation position (presentation distance) of the target with respect to the subject eye. In this case, for example, as a configuration in which the presentation position (presentation distance) of the target is optically changed, a light source (for example, the display) emitting the target light flux may be moved in the optical axis direction. In addition, in this case, for example, the optical elements (for example, a spherical lens) arranged in the optical path may be moved in the optical axis direction. Of course, the calibration optical system may have a configuration in of a combination of the configuration for controlling optical elements and the configuration for moving optical elements arranged in the optical path in the optical axis direction.

For example, the calibration optical system may be an optometry unit (folopter) that switches the arrangement of the optical elements arranged in front of the subject eye. For example, the optometry unit may be configured to include a pair of left and right lens chamber units in which the optical elements are switched and arranged in an examination window. For example, the optometry unit may include a lens disc in which a plurality of optical elements are arranged on the same circumference and a driver which rotates the lens disc, and may electrically switch the optical elements by driving by the driver (for example, a motor).

For example, the calibration optical system may be configured to change the optical characteristics of the target light flux by arranging the optical elements between the optical member for guiding the target light flux from the projection optical system toward the subject eye and the light source of the projection optical system to control the optical elements. That is, the calibration optical system may have a configuration of a phantom lens refractometer (phantom calibration optical system). In this case, for example, the target light flux corrected by the calibration optical system is guided to the subject eye via the optical member.

For example, in the present embodiment, the calibration optical system includes a calibration optical system for the right eye and a calibration optical system for left eye that are provided at right and left in a pair. For example, in the calibration optical system for right eye and the calibration optical system for left eye, a member configuring the calibration optical system for right eye and a member configuring the calibration optical system for left eye may be the same member. In addition, for example, in the calibration optical system for right eye and the calibration optical system for left eye, at least a part of the member configuring the calibration optical system for right eye and the member configuring the calibration optical system for left eye may be different from each other. For example, in the calibration optical system for right eye and the calibration optical system for left eye, at least a part of the member configuring the calibration optical system for right eye and the member configuring the calibration optical system for left eye may be used for both. In addition, for example, in the calibration optical system for right eye and the calibration optical system for left eye, the member configuring the calibration optical system for right eye and the member configuring the calibration optical system for left eye may be separately provided, respectively.

<Information Processor>

For example, the information processor accepts various operation instructions from the examiner or the examinee. For example, as the information processor, at least any one of a PC, a server, a mobile terminal, a smartphone, and the like may be used. Of course, the information processor is not limited to the configuration described above. For example, at least one of various information processors capable of processing various information can be used as the information processor.

For example, the information processor may include an input unit (for example, the operation unit 23) for the examiner or the examinee to input various operation instructions. For example, at least one of user interfaces such as a touch panel, a mouse, a joystick, a keyboard, and a microphone may be used as the input unit.

<Target Presentation Device>

For example, in a plurality of subjective optometry devices, at least any one of the subjective optometry devices may include a target presentation device for emitting the target light flux. For example, the target presentation device may include a target presentation unit (for example, the target presentation unit 16) that emits the target light flux, and the target light flux emitted from the target presentation unit may be projected toward the subject eye. For example, the target presentation device may include a projection optical system having at least one or more optical members that project the target light flux toward the subject eye.

For example, as the target presentation unit, display may be used. For example, the display may be any of a liquid crystal display (LCD), an organic electro luminescence (EL), and the like. For example, on the display, an examination target such as a Randold ring target is presented.

In addition, For example, a digital micromirror device (DMD) may be used as the target presentation unit. Generally, the DMD has high reflectance and is bright. Therefore, the amount of light of the target light flux can be maintained as compared to the case of using a liquid crystal display using polarized light.

In addition, for example, the target presentation unit may be configured to include a visible light source for target presentation and a target board. In this case, for example, the target board is a rotatable disk board and has a plurality of targets. For example, the plurality of target include a target for visual acuity examination target used at the time of subjective measurement, and the like. For example, in the visual acuity examination target, the targets for each visual acuity value (visual acuity values 0.1, 0.3, . . . , 1.5) are prepared. For example, the target board is rotated by a motor or the like, and the target is switched and arranged on the optical path where the target light flux is guided to the subject eye. Of course, a target presentation unit other than the above configuration may be used as the target presentation unit that projects the target light flux.

For example, the projection optical system may include at least one or more optical members that project the target light flux toward the subject eye. For example, the projection optical system may include an optical member (for example, a concave mirror 13) that guides an image of the target light flux emitted from the target presentation unit to the subject eye so as to be an optically predetermined examination distance.

For example, the projection optical system projects the target light flux toward the subject eye by causing the target light flux emitted from the target presentation unit to be incident so as to be shifted with respect to the optical axis of the optical member. In this case, for example, the target presentation unit may be arranged by inclining the normal direction of the target presentation unit with respect to the screen with respect to the optical axis of the optical member.

For example, at least one of a concave mirror, a lens, and the like may be used as the optical member. For example, when the optical member is a concave mirror, the projection optical system may include a reflection member that causes the target light flux emitted by the target presentation unit to be reflected toward the concave mirror and guides the target light flux reflected by the concave mirror to the outside from the inside of the housing. With such a configuration, the number of members of the projection optical system can be reduced and it is possible to further reduce the space of the subjective optometry device. Of course, the projection optical system is not limited to the configuration described above, and any configuration may be used as long as the target light flux emitted from the target presentation unit is incident so as to be shifted with respect to the optical axis of the optical member and the target light flux is projected toward the subject eye.

For example, any one of a mirror (for example, a total reflection mirror, a half mirror, and the like), a prism, and the like may be used as the reflection member. Of course, the reflection member is not limited to this, and any member that guides the target light flux toward the subject eye may be used.

For example, the projection optical system may include a projection optical system for right eye and a projection optical system for left eye that are provided at right and left in a pair. In this case, for example, a pair of target presentation units that are provided at right and left may be used. For example, in the projection optical system for right eye and the projection optical system for left eye, the members configuring the projection optical system for right eye and the members configuring the projection optical system for left eye may be the same. In addition, for example, in the projection optical system for right eye and the projection optical system for left eye, at least a part of the members configuring the projection optical system for right eye and the members configuring the projection optical system for left eye may be different from each other. For example, in the projection optical system for right eye and the projection optical system for left eye, at least a part of the members configuring the projection optical system for right eye and the members configuring the projection optical system for left eye may be shared by each other. In addition, for example, in the projection optical system for right eye and the projection optical system for left eye, the members configuring the projection optical system for right eye and the members configuring the projection optical system for left eye may be separately provided.

EXAMPLE

Figure 1:
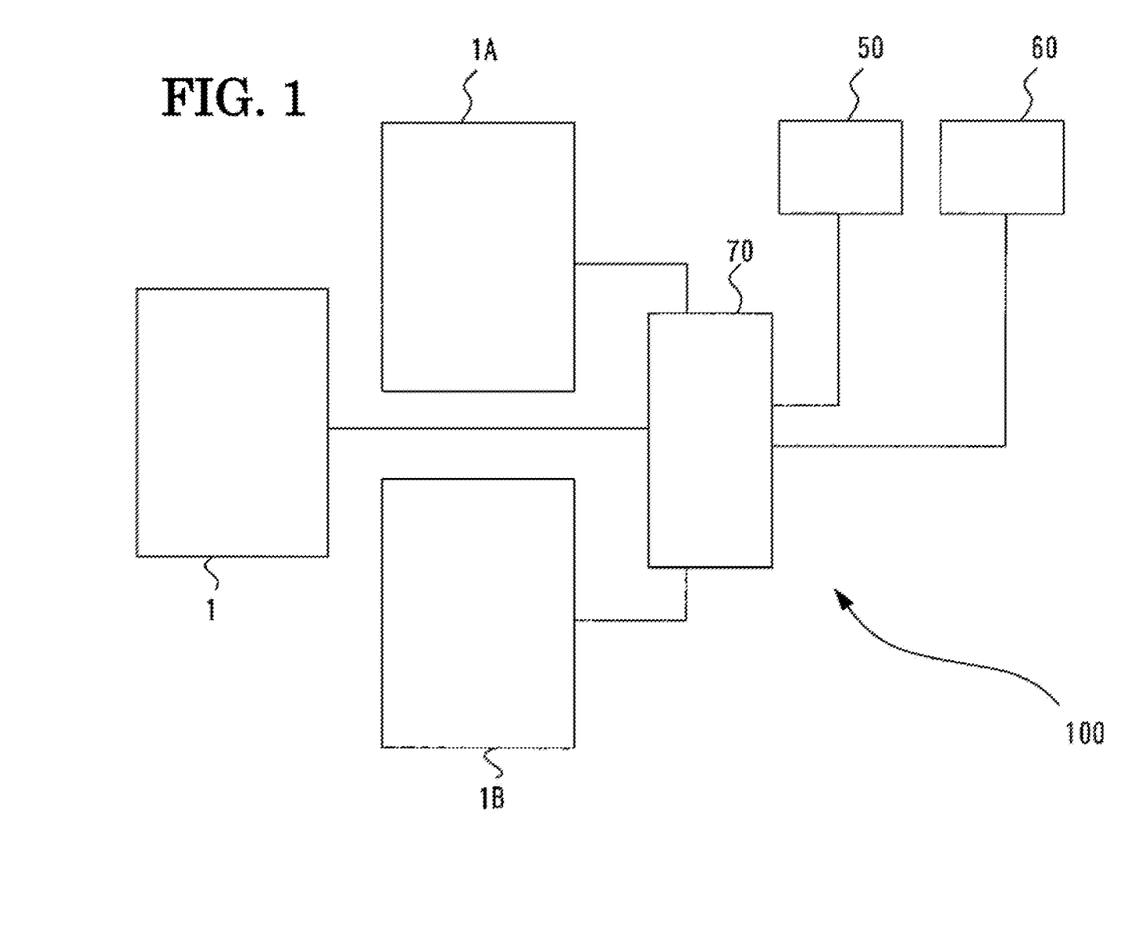
FIG. 1 is a block diagram showing a schematic configuration of a subjective optometry system.
Figure 2:
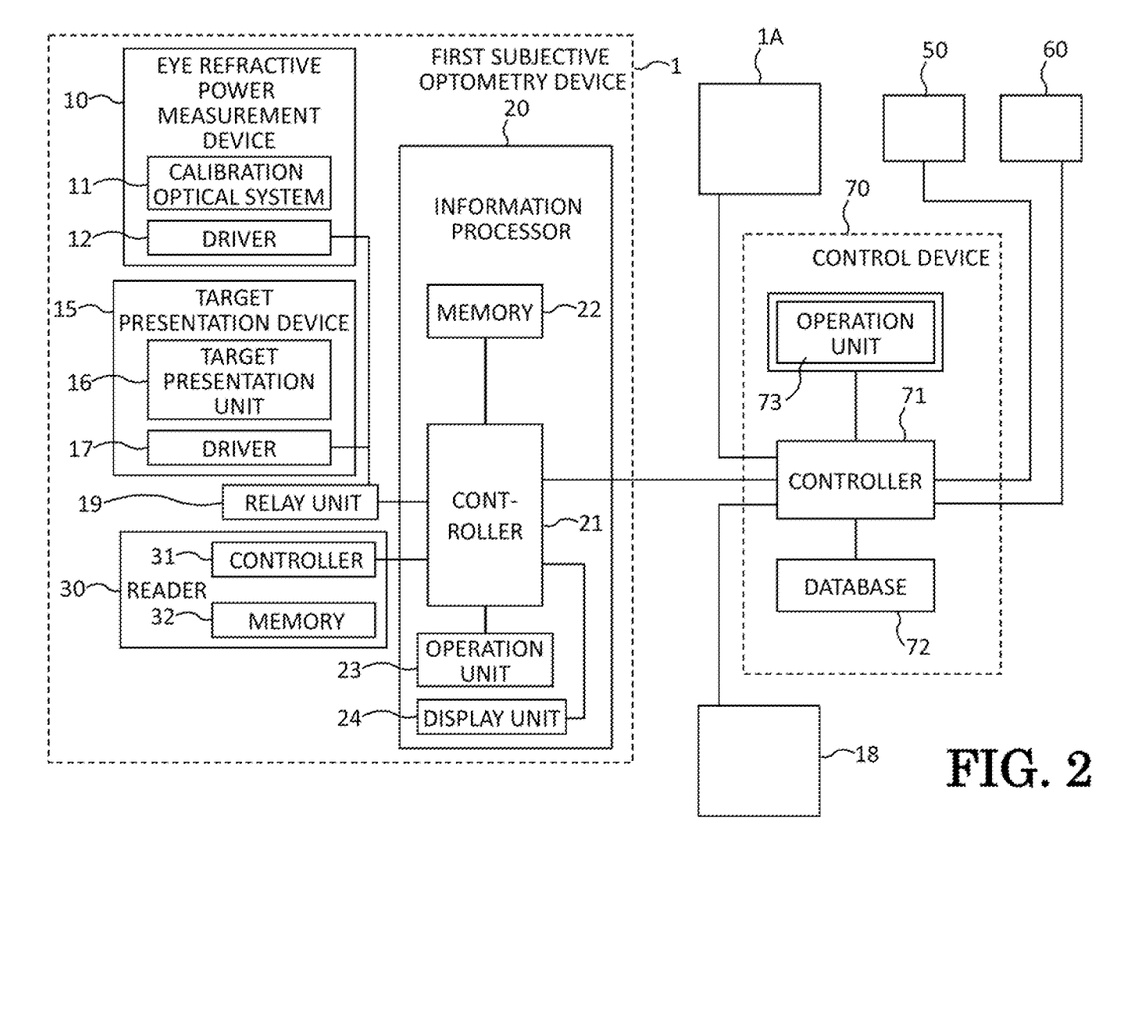
FIG. 2 is a block diagram showing a schematic configuration of each device of the subjective optometry system.

Hereinafter, one of the typical examples in the present disclosure will be described with reference to the drawings. For example, FIG. 1 is a block diagram showing a schematic configuration of a subjective optometry system. FIG. 2 is a block diagram showing a schematic configuration of each device of the subjective optometry system.

For example, as shown in FIG. 1, a subjective optometry system 100 in the present embodiment includes a first subjective optometry device 1, a second subjective optometry device 1A, a third subjective optometry device 1B, an objective measurement device 50, a lens characteristics measurement device 60, and a control device 70.

For example, the first subjective optometry device 1, the second subjective optometry device 1A, and the third subjective optometry device 1B are used for subjectively measuring the optical characteristics of the subject eye. In the present example, the optical characteristics of the subject eye measured by the first subjective optometry device 1, the second subjective optometry device 1A, and the third subjective optometry device 1B is eye refractive power. For example, the measured eye refractive power may be at least one of the spherical power and the cylindrical power, the astigmatic axis angle of the subject eye, and the like.

In the present example, a case where the first subjective optometry device 1, the second subjective optometry device 1A, and the third subjective optometry device 1B have the same configuration will be described as an example. Of course, at least a part of the configurations of the first subjective optometry device 1, the second subjective optometry device 1A, and the third subjective optometry device 1B may be different from each other.

For example, the objective measurement device 50 and the lens characteristics measurement device 60 are connected to the control device 70 in a communicable state via a network (for example, the Internet). More specifically, for example, the objective measurement device 50 and the lens characteristics measurement device 60 are connected to a controller 71 of the control device 70 in a communicable state. In addition, each subjective optometry device of the first subjective optometry device 1, the second subjective optometry device 1A, and the third subjective optometry device 1B is connected to the control device 70 in a communicable state via the network. For example, various standards such as LAN can be adopted as the connection standard between various devices.

For example, the control device 70 manages various controls of the subjective optometry system 100. As the control device 70, various information processors (for example, at least one of a PC, a server, a mobile terminal, and the like) can be used. The control device 70 includes the controller (for example, a CPU) 71 that manages the control, a database 72 that stores various data, and an operation unit 73 for setting various subjective optometry systems.

For example, as the operation unit 73, at least one of a user interface such as a touch panel, a mouse, a joystick, and a keyboard may be used. In the present example, the operation unit 73 is a touch panel. Therefore, in the present example, a display is used as the operation unit 73, and the display also functions as the operation unit. For example, the database 72 stores at least any data of the objective measurement data and the previous glass data in association with each identifier. The configuration of the control device 70 can also be changed. First, a plurality of devices may work together to function as the control device 70. For example, the control device that manages various controls in the subjective optometry system 100 and the control device provided with the database 72 may be different devices. For example, the controller 71 and the database 72 are connected to each other. In addition, for example, the controller 71 and the operation unit 73 are connected to each other.

For example, the objective measurement device 50 objectively measures the optical characteristics of the subject eye. For example, examples of the optical characteristics of the subject eye objectively measured include the eye refractive power (for example, the spherical power, the astigmatic power, the astigmatic axis angle, and the like), the polarization characteristics, and the like. In the present embodiment, the objective measurement device which measures the eye refractive power of the subject eye will be described as an example.

For example, as the lens characteristics measurement device 60, a lens meter is used. For example, the lens meter is used for measuring the optical characteristics of glass lenses. For example, examples of the optical characteristics of the glass lens measured by the lens meter include the refractive power (for example, the spherical power, the astigmatic power, astigmatic axis angle, and the like), the polarization characteristics, and the like.

Next, the configuration of the subjective optometry device will be described. In the present example, the second subjective optometry device 1A and the third subjective optometry device have the same configuration as the first subjective optometry device the description of the configuration of the second subjective optometry device 1A and the third subjective optometry device 1B will be omitted. The configuration of the subjective optometry device will be described below with the first subjective optometry device as an example.

For example, the first subjective optometry device 1 includes an eye refractive power measurement apparatus 10, a target presentation device 15, a relay unit 19, an information processor 20, and a reader 30.

For example, the eye refractive power measurement apparatus 10 includes a calibration optical system 11 and a driver 12. The calibration optical system 11 changes the optical characteristics of the target light flux presented to the subject eye. In the present example, for example, the calibration optical system 11 changes at least one of the spherical power, the cylindrical power, the astigmatic axis angle, the polarization characteristics, the aberration amount of the target light flux, and the like as the optical characteristics. As an example, the calibration optical system 11 in the present example changes the optical characteristics of the target light flux by switching the optical elements arranged in the examination window in front of the subject eye among a plurality of optical elements. In the calibration optical system 11 in the present embodiment, a lens disc for the left eye and a lens disc for the right eye in which a plurality of optical elements are arranged on the same circumference are used. Each of the lens disc for the left eye and the lens disc for the right eye may be one or more. As the optical elements, for example, at least one of a spherical lens, a cylindrical lens, a cross cylinder lens, a rotary prism, a wave surface modulation element, and the like may be used. The driver 12 changes the optical characteristics of the target light flux by driving the calibration optical system 11. The driver 12 in the present embodiment drives the calibration optical system 11 by rotating each of the lens disc for the left eye and the lens disc for the right eye and switching the optical elements arranged in the examination window. As the driver 12, for example, a step motor or the like can be used. The driver 12 is driven in response to a drive signal.

For example, the target presentation device 15 presents an examination target (for example, at least one of the Randold ring target, characters, and the like) to the subject eye, and switches the examination target to be presented to the subject eye. Specifically, the target presentation device 15 includes a target presentation unit 16 and a driver 17. The target presentation unit 16 presents the examination target to the subject eye. As the target presentation unit 16, for example, at least one a space-saving target projection device that projects an examination target onto a subject eye via a concave mirror, a chart projector that projects an examination target onto a screen, a display that displays the examination target, and the like, can be adopted. The target presentation unit 16 is arranged at substantially the same height as the eye refractive power measurement apparatus 10 such that the distance from the subject eye becomes optically a predetermined distance. The driver 17 switches the examination target presented to the subject eye by driving the target presentation unit 16. The driver 17 is driven in response to a drive signal.

The information processor 20 is used to operate the first subjective optometry device 1. For example, in the present example, a PC is used as the information processor 20. Of course, the information processor that can function as the information processor 20 is not limited to the PC. For example, a server, a mobile terminal, a smartphone, or the like may be used as an information processor.

For example, the information processor 20 is arranged at a base (for example, an eyeglass store or a hospital) where the subjective optometry for the examinee is performed. The information processor 20 includes a controller 21, a memory (storage unit) 22, an operation unit 23, and a display unit (display) 24. The controller 21 manages the control of the information processor 20. The memory 22 can store a program, various data, and the like. In the present example, the optometry control program is stored in the memory 22. For example, as the operation unit 23, at least one of a user interface such as a touch panel, a mouse, a joystick, and a keyboard may be used. For example, the information processor 20 is connected to the first subjective optometry device 1 (specifically, the relay unit 19 of the first subjective optometry device 1) in a communicable state.

For example, the relay unit 19 relays the drive signal between the information processor 20 and the drivers 12 and 17. For example, the relay unit 19 in the present example converts the operation signal received from the information processor 20 into a drive signal that can control the drivers 12 and 17, and transmits the operation signal to the drivers 12 and 17. Furthermore, when receiving one operation signal for driving two drivers 12 and 17 from the information processor 20, the relay unit 19 in the present example converts one received operation signal into two drive signals for driving each of the two drivers 12 and 17, respectively, and transmits the drive signals to each of the two drivers 12 and 17. For example, the information processor 20 is connected to the first subjective optometry device 1 (specifically, the relay unit 19 of the first subjective optometry device 1) in a communicable state. In addition, for example, the information processor 20 is connected to the control device 70 (specifically, the controller 21 of the information processor 20 is connected to the controller 71 of the control device 70) in a communicable state. Therefore, for example, the information processor 20 is connected to the database 72 in a communicable state via the controller 71. For example, the information processor 20 may include the relay unit 19. That is, the information processor 20 and the relay unit 19 may be integrally provided.

For example, the reader 30 is connected to the information processor 20, reads the identifier prepared for each examinee, and outputs the information about the read identifier to the information processor 20. For example, as the reader 30, an identifier reader (for example, a QR code (registered trademark) reader, a barcode reader, an identification hole reader, and the like) corresponding to the identifier being used is used.

For example, the reader 30 includes a controller 31 and a memory (storage unit) 32. The controller 31 manages the control of the reader 30. The memory 32 can store programs, various data, and the like. In the present example, the reading control program is stored in memory 32. For example, the reader 30 is connected to the first subjective optometry device 1 (specifically, the information processor 20 of the first subjective optometry device 1) in a communicable state. More specifically, for example, the controller 31 of the reader 30 is connected to the controller 21 of the information processor 20 in a communicable state.

The subjective optometry system 100 can be appropriately constructed by any system according to the intended use. That is, the connection destination between each device can be connected to any member to construct a subjective optometry system.

<Operation>

Hereinafter, an operation using the subjective optometry system 100 in the present example will be described. In the following description of the operation, the operation using the first subjective optometry device 1 as the subjective optometry device will be described as an example. Of course, in other subjective optometry devices, an operation same as that of the first subjective optometry device 1 can be performed. In the present example, a case where both the objective measurement data and the previous glass data are acquired will be described as an example.

First, an identifier for an examinee on which the subjective measurements are performed is issued by an identifier issuing device (not shown). In the present example, for example, the identifier is issued by being printed on paper. For example, after the identifier is issued, the identifier may be managed in the database for each examinee as an identifier for the examinee (that is, an ID for the examinee). That is, after the identifier is issued, when the examination is executed to the examinee on a different day, the subsequent examination may be performed using the identifier issued in the past instead of issuing a new identifier. Of course, every time the examination is completed, the identifier may be reissued and the examination may be performed.

For example, when the identifier is issued, the lens characteristics measurement device 60 is used to measure the glasses worn by the examinee for acquiring previous glass data. In the present example, a case where the previous glass data obtained by measuring the refractive power of the glass lens is used will be described as an example. The measurement by the lens characteristics measurement device 60 may be omitted as appropriate.

For example, the issued identifier is read by a reader (not shown) connected to the lens characteristics measurement device 60. Next, the lens characteristics measurement device 60 is driven and the previous glass data is acquired. When the previous glass data is acquired, the identifier read by the reader is transmitted to the controller 71 of the control device 70 together with the previous glass data. For example, when the controller 71 receives and acquires the previous glass data and the identifier, the previous glass data and the identifier are stored in the database 72 in association with each other.

Next, the subject eye is measured using the objective measurement device 50, and the objective measurement data of the subject eye is acquired. In the present example, a case where the objective measurement data obtained by measuring the eye refractive power of the subject eye is used will be described as an example. The measurement by the objective measurement device 50 may be omitted as appropriate.

For example, the issued identifier is read by a reader (not shown) connected to the objective measurement device 50. Next, the objective measurement device 50 is driven and the objective measurement data is acquired. When the objective measurement data is acquired, the identifier read by the reader is transmitted to the controller 71 of the control device 70 together with the objective measurement data. For example, the controller 71 receives and acquires the objective measurement data and the identifier, the objective measurement data and the identifier are stored in the database 72 in association with each other.

By performing the processing described above, the objective measurement data and the previous glass data are stored in the database 72 for each examinee in association with the issued identifier.

Next, the subjective measurement is performed. For example, in the present example, before starting the subjective measurement of the optical characteristics of the subject eye by the first subjective optometry device 1, the initial value of the calibration optical system 11 used on an occasion of subjectively measuring the optical characteristics of the subject eye is set based on at least any one of the objective measurement data and the previous glass data using at least any one of the objective measurement device 50 and the lens characteristics measurement device 60.

For example, in the first subjective optometry device 1, when the measurement is started, the examiner or the examinee holds the subject the identifier over the reader 30 to read the identifier. For example, the controller 31 of the reader 30 outputs (transmits) the information about the read identifier to the controller 21 of the information processor 20. For example, when receiving the identifier information, the controller 21 connects to the database 72 via the controller 71 of the control device 70. The controller 21 acquires the objective measurement data and the previous glass data corresponding to the identifier from the database 72 based on the identifier. That is, the data are acquired from the database 72 via the information processor 20 connected to the reader 30 that read the identifier.

For example, when the data are acquired from the database 72, the controller 21 displays a selection screen on the display unit 24 for selecting which of the data will be based on for setting the initial value. For example, when the operation unit 23 is operated by the examinee or the examiner, and any data of the objective measurement data and the previous glass data is selected, the initial value is set based on the selected data. In the present example, the initial value may be set based on the selected data, and the identifier may be set in the first subjective optometry device 1 as the ID of the examinee. In the present example, a case where the objective measurement data is selected will be described as an example.

For example, the controller 21 sets the acquired objective measurement data as the initial value of the calibration optical system 11. For example, in the present example, a case using the eye refractive power (for example, the spherical power, the astigmatic power, and the astigmatic axis angle) as the optical characteristics used for setting the initial value, will be described as an example. In the present example, the case of using the eye refractive power as the optical characteristics used for setting the initial value is described but the present example is not limited to this. For example, other optical characteristics may be used as the optical characteristics used for setting the initial value. In addition, for example, at least any of the spherical power, the astigmatic power, and the astigmatic axis angle may be used as the eye refractive power used for setting the initial value.

For example, the controller 21 drives the driver 12 based on the objective measurement data, controls the drive of the calibration optical system 11 to set the initial value. In the present example, for example, the calibration optical system 11 is controlled so as to correct a refraction error of the subject eye based on the eye refractive power which is the objective measurement data of the subject eye. For example, when the calibration optical system 11 is controlled and the initial value setting is completed, the subjective measurement is started. In subjective measurement, the calibration power of the calibration optical system 11 is changed, and the subjective optical characteristics of the subject eye are obtained. That is, the subjective measurement is performed from the state where the setting of the initial value is completed. For example, when the subjective measurement is completed, the controller 21 stores the subjective measurement data acquired by the subjective measurement in the database 72 together with the identifier and in association with the identifier.

As described above, for example, the subjective optometry system in the present example includes a plurality of subjective optometry devices that are a plurality of subjective optometry devices used for subjectively measuring the optical characteristics of the subject eye, and each includes the calibration optical system that changes the optical characteristics of the target light flux presented to the subject eye, the information processor for operating the subjective optometry device, and the reader that is connected to the information processor, reads the identifier prepared for each examinee, and outputs the information about the read identifier to the information processor. In addition, for example, the subjective optometry system includes a database in which at least any data of the objective measurement data and the previous glass data are stored in association with each identifier. In addition, for example, the information processor in the subjective optometry system acquires at least one of the objective measurement data and the previous glass data corresponding to the identifier from the database based on the identifier received from the reader, and sets the initial value of the calibration optical system when subjectively measuring the optical characteristics of the subject eye based on at least one of the objective measurement data and the previous glass data. As described above, for example, by connecting the reader to the information processor of each subjective optometry device, the identifier information read by the reader is output to the connected information processor, since the information processor that received the identifier information acquires the data corresponding to the identifier, the subjective optometry system can easily grasp the information processor of the subjective optometry device that requires the data corresponding to the identifier. In other words, by connecting the subjective optometry system to the database via the information processor connected to the reader that reads the identifier, it is possible to easily grasp the information processor of the subjective optometry device that requires the data corresponding to the identifier. Therefore, in the subjective optometry system in which a plurality of subjective optometry devices can be connected to the database, when at least any data of the objective measurement data and the previous glass data is acquired from the database, it is possible to suppress a problem of not knowing the information processor of the subjective optometry device that requires the data. That is, even in a subjective optometry system in which the information processor of a plurality of subjective optometry devices can be connected, in the processing for the identifier read by the reader, it is possible to easily grasp the subjective optometry device on which the initial setting (setting the initial value) should be executed.

In addition, for example, by collectively managing the information on the examinee in association with the identifier, various data can be easily acquired based on the identifier, and thus, it is possible to easily set the initial value of the calibration optical system used on an occasion of subjectively measuring the optical characteristics of the subject eye. Therefore, erroneous input of examinee information and an effort of the examiner to input the data can be suppressed, and thus, it is possible to accurately and smoothly start the subjective measurement in each subjective optometry device.

In addition, for example, when receiving the identifier information, the information processor of the subjective optometry system in the present example automatically may acquire at least one of the objective measurement data and the previous glass data corresponding to the identifier from the database, and may automatically set the initial value of the calibration optical system based on at least one of the objective measurement data and the previous glass data. In this way, for example, when the reader reads the identifier, since the acquisition of the data can be performed quickly and the initial value can be set, it is possible to easily set to start the subjective measurement without operating the information processor by the examinee or examiner. In particular, when the examinee uses the information processor to perform the examination by himself (self-examination), since it is difficult to understand the state of the information processor and the operation method, this technology is useful.

In addition, for example, the subjective optometry system in the present example includes the data acquisition device that acquires at least any data of the objective measurement data and the previous glass data, and the database setting device that stores at least any data of the objective measurement data and the previous glass data acquired by the data acquisition device in the database in association with the identifier. In this way, for example, for each examinee, the identifier and the data are stored in the database in a state of being appropriately associated with each other. Therefore, by reading the identifier, appropriate data is acquired for each examinee.

Modification Example

In the description above, a configuration using at least any data of the objective measurement data and the previous glass data as the data corresponding to the identifier has been described as an example, but the present disclosure is not limited to this. Furthermore, the subjective measurement data which is a past subjective measurement result of the examinee performing the subjective measurement may be used as the data.

In this case, for example, the subjective measurement data measured on different days (measured in the past) may be stored in the database in association with each identifier. For example, the information processor may acquire the subjective measurement data corresponding to the identifier from the database based on the identifier received from the reader, and the initial value of the calibration optical system used on an occasion of subjectively measuring the optical characteristics of the subject eye may be set based on the subjective measurement data. With such a configuration, for example, the subjective measurement data can be used instead of the previous glass data and the objective data, it is possible to set the initial value smoothly.

More specifically, for example, the identifier is issued for each examinee. For example, in the first subjective optometry device 1, when the measurement is started, the examiner or the examinee holds the subject the identifier over the reader 30 to read the identifier. Thereafter, for example, in the first subjective optometry device 1, the optical characteristics of the subject eye are subjectively measured. When the subjective measurement is completed and the subjective measurement data is acquired, the identifier read by the reader 30 is transmitted to the controller 71 of the control device 70 together with the subjective measurement data. For example, when receiving and acquiring the subjective measurement data and the identifier, the controller 71 stores the subjective measurement data and the identifier in the database 72 in association with each other. By performing the processing described above, the subjective measurement data is stored in the database 72 in association with the identifier issued for each examinee. As the subjective optometry device, a subjective optometry device different from the first subjective optometry device 1 may be used.

Then, for example, when performing the subjective measurement of the examinee again on a different day, the examiner or the examinee causes the reader 30 to read the identifier issued for each examinee. For example, in the first subjective optometry device 1, when the measurement is started, the examiner or the examinee holds the subject the identifier over the reader 30 to read the identifier. For example, the controller 31 of the reader 30 outputs (transmits) the information about the read identifier to the controller 21 of the information processor 20. For example, when receiving the identifier information, the controller 21 connects to the database 72 via the controller 71 of the control device 70. The controller 21 acquires the subjective measurement data corresponding to the identifier from the database 72 based on the identifier.

For example, when the subjective measurement data is acquired from the database 72, the controller 21 sets the acquired subjective measurement data as the initial value of the calibration optical system 11. For example, when the subjective measurement data is acquired together with at least any data of the objective measurement data and the previous glass data, the subjective measurement data may be preferentially set as the initial value. Of course, other data may be preferentially set as the initial value. The data used for setting the initial value may be selected by the examiner after the acquisition of the data, or may be set in advance. Of course, the initial value may be set using a plurality of data (for example, using an average value of the plurality of data).

In the description above, as the data, in addition to at least any data of the objective measurement data and the previous glass data, the subjective measurement data can be used as the data corresponding to the identifier as an example, but the present disclosure is not limited to this. At least any of the objective measurement data, the previous glass data, and the subjective measurement data may be used as the data corresponding to the identifier. For example, when performing the subjective measurement of the examinee again on a different day, the examiner or the examinee causes the reader 30 to read the identifier issued for each examinee. For example, in the first subjective optometry device 1, when the measurement is started, the examiner or the examinee holds the subject the identifier over the reader 30 to read the identifier. For example, the controller 31 of the reader 30 outputs (transmits) the information about the read identifier to the controller 21 of the information processor 20. For example, when receiving the identifier information, the controller 21 connects to the database 72 via the controller 71 of the control device 70. The controller 21 acquires at least any data of the objective measurement data, the previous glass data, and the subjective measurement data corresponding to the identifier from the database 72 based on the identifier.

For example, when at least any data of the objective measurement data, the previous glass data, and the subjective measurement data is acquired from the database 72, the controller 21 displays the selection screen on the display unit 24 for selecting which of the data will be based on for setting the initial value. For example, the operation unit 23 is operated by the examinee or the examiner, and when any data is selected from the objective measurement data, the previous glass data, and the subjective measurement data, the initial value is set based on the selected data.

In the present example, a case where the subjective optometry system 100 in which the database 72 is provided in the control device 70 is described as an example, but the present application is not limited to this. Any members can be set as the database. Hereinafter, the database settings will be described below. In the present example, a case where the database setting is performed using the operation unit 73 of the control device 70 will be described as an example. Of course, any configuration can be used for setting the database.

Figure 3:
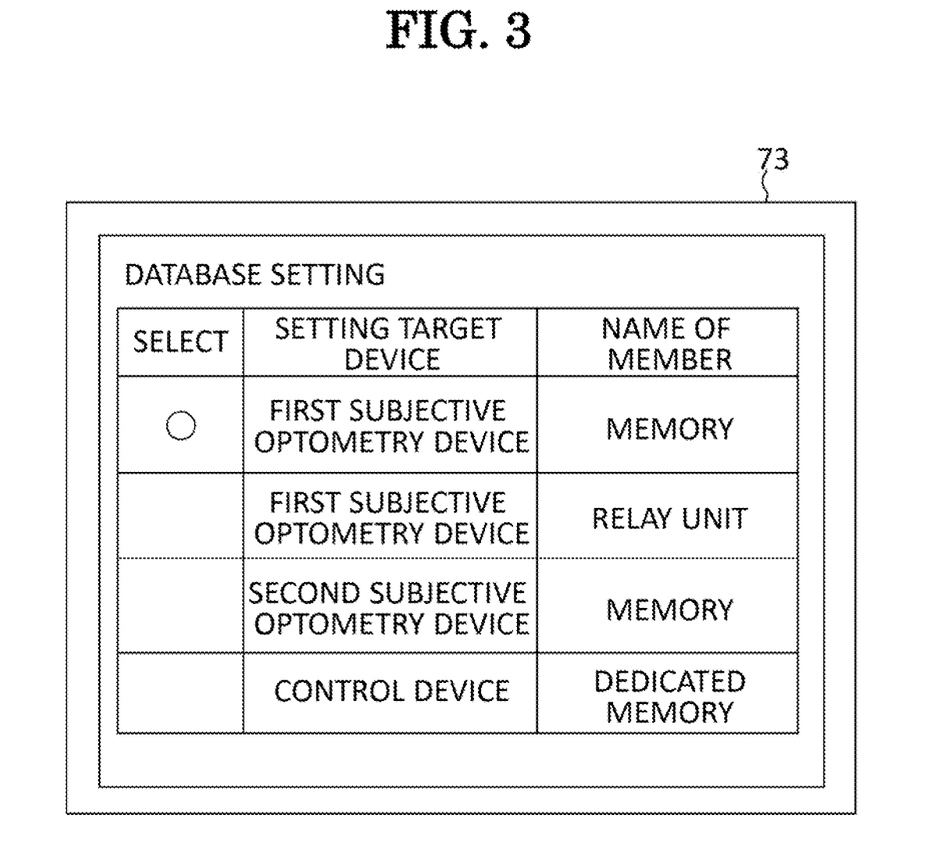
FIG. 3 is a diagram showing a database setting screen.

For example, FIG. 3 is a diagram showing a database setting screen. For example, the operation unit 73 is operated by the constructor of the subjective optometry system and the database setting screen is selected. For example, the controller 71 displays a database setting screen as shown in FIG. 3 on the display screen of the operation unit 73. As shown in FIG. 3, a list of members (names of members) in each device that constructs the subjective optometry system 100 (for example, the first subjective optometry device 1, the second subjective optometry device 1A, the third subjective optometry device 1B, the control device 70, and the like) that can be used as the database is displayed in the database setting screen. For example, the constructor selects the memory to set as the database from the list. For example, when the operation unit 73 is operated by the constructor and the memory to set as the database, the controller 71 sets the selected memory as the database.

Figure 4:
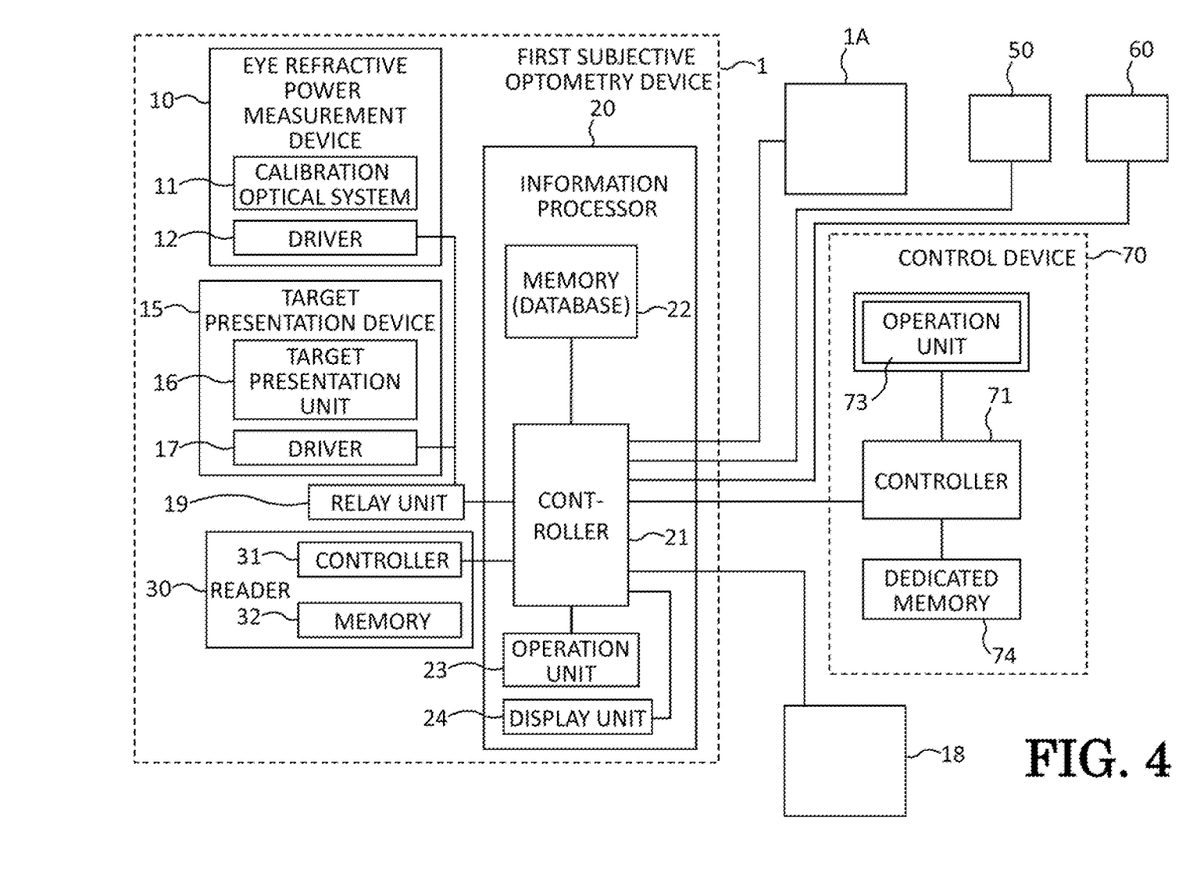
FIG. 4 is a block diagram showing a schematic configuration of a subjective optometry system in a modification example.

For example, FIG. 4 is a block diagram showing a schematic configuration of the subjective optometry system in the modification example. For example, FIG. 4 is a block diagram illustrating a case where memory 22 of the information processor 20 is set as the database. In the subjective optometry system 100 in FIG. 2 in the present example, a case where dedicated memory 74 of the control device 70 in FIG. 4 is set as the database is shown as an example.

As shown in FIG. 4, the memory 22 of the information processor 20 is set as the database, and each subjective optometry device (for example, the second subjective optometry device 1A, the third subjective optometry device 1B, and the like), the objective measurement device 50, the lens characteristics measurement device 60 are connected to the information processor 20 (specifically, the controller 21 of the information processor 20). With such a configuration, for example, a subjective optometry system can be constructed with a simple configuration without separately requiring a dedicated configuration (for example, the dedicated memory 74, and the like) for providing the database.

For example, the relay unit 19 of the first subjective optometry device 1 may be used as the database. In this case, for example, each subjective optometry device (for example, the second subjective optometry device 1A, the third subjective optometry device 1B, and the like) is connected to the relay unit 19. With such a configuration, for example, by the relay unit also serving as the memory, even when various types of information processors that are different for each subjective optometry device are used, it is possible to easily acquire the data corresponding to the identifier.

As described above, for example, in the subjective optometry system in the present modification example, each of the plurality of subjective optometry devices includes the memory and the selection unit that can selectively set a memory used as the database among the dedicated memory which is different from the memory and is dedicated to setting the database, and the memories of the subjective optometry devices. With such a configuration, for example, when setting the database, the configuration for setting the database can be changed depending on a place where the plurality of subjective optometry devices are installed, and it is possible to construct the appropriate subjective optometry system according to usage of the examiner. As an example, in a case of a subjective optometry system in which a plurality of subjective optometry devices are arranged in a common building (for example, a store, a hospital, and the like) (for example, cooperation in a common building), by setting the database in the memory of the subjective optometry device, it is possible to construct the subjective optometry system with a simple configuration without requiring a separate configuration for providing a database. In addition, as an example, in a case of a subjective optometry system in which a plurality of subjective optometry devices are arranged in different buildings (for example, distant stores, distant hospitals, and the like) (for example, cooperation outside the common building), by setting the database in the dedicated memory provided for the database in a dedicated manner, it is possible to smoothly acquire the data without imposing a load on the memory of the predetermined subjective optometry device.

Figure 5:
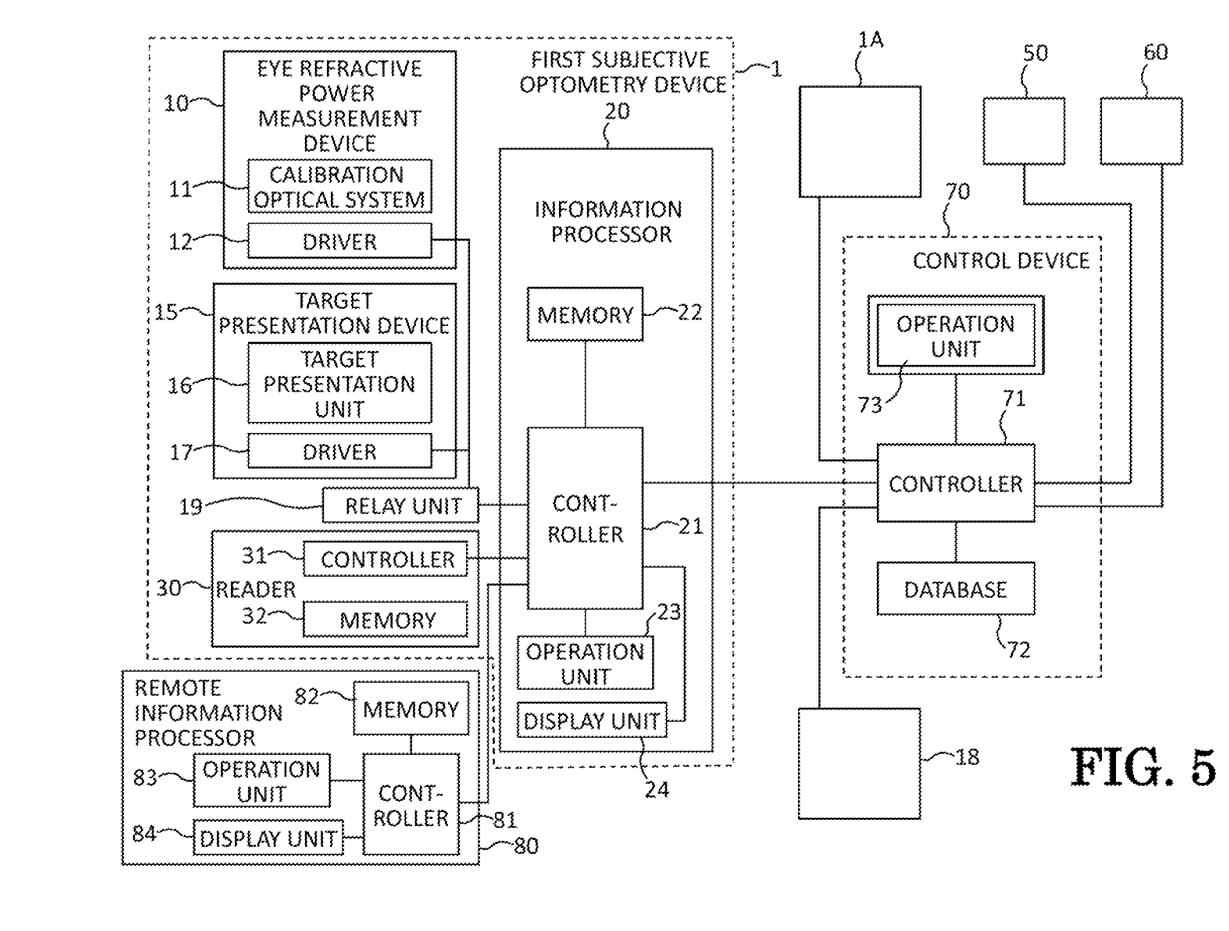
FIG. 5 is a block diagram showing a schematic configuration of a subjective optometry system having a remote information processor.

In the present example, for example, the subjective optometry system may include a remote information processor that can operate the subjective optometry device from the remote access destination. FIG. 5 is a block diagram showing the schematic configuration of a subjective optometry system having the remote information processor. Hereinafter, the subjective optometry system having the remote information processor will be described.

For example, the remote information processor 80 is arranged at a remote access destination (for example, a remote location or the like). For example, the remote information processor 80 includes a controller 81, a memory (storage unit) 82, an operation unit 83, and a display unit (display) 84. For example, the controller 81 manages the control of the remote information processor 80. The memory 82 can store programs, various data, and the like. For example, as the operation unit 83, at least one of a user interface such as a touch panel, a mouse, a joystick, and a keyboard may be used. For example, the information processor 80 is connected to the first subjective optometry device 1 (specifically, the controller 21 of the first subjective optometry device 1) in a communicable state.

In the present example, for example, the remote information processor 80 can remote-access the information processor 20. For example, the remote information processor 80 can operate at least one of a subjective optometry devices among a plurality of subjective optometry devices via the information processor 20. For example, in the present example, the remote information processor 80 has a configuration which can operate the information processor 20 of the first subjective optometry device 1 and can set the initial value of the calibration optical system 11.

The description will be made in more detail. In the description below, a case where the objective measurement data and the previous glass data are acquired as the data acquired from the database will be described as an example. For example, in the first subjective optometry device 1, when the measurement is started, the examiner or the examinee holds the subject the identifier over the reader 30 to read the identifier. For example, the controller 31 of the reader 30 outputs (transmits) the information about the read identifier to the controller 21 of the information processor 20. For example, when receiving the identifier information, the controller 21 connects to the database 72 via the controller 71 of the control device 70. The controller 21 acquires the objective measurement data and the previous glass data corresponding to the identifier from the database 72 based on the identifier.

For example, when the data is acquired from the database 72, the controller 21 outputs (transmits) the data to the remote information processor 80 (specifically, the controller 81). For example, the controller 81 receives the objective measurement data and the previous glass data output from the controller 21. For example, the controller 81 displays the received objective measurement data and previous glass data on the display unit 84. For example, the controller 81 displays a selection screen on the display unit 84 for selecting for selecting which of the objective measurement data or the previous glass data will be based on for setting the initial value.

For example, when the operation unit 83 is operated by the examiner and any data of the objective measurement data and the previous glass data is selected, the initial value is set based on the selected data. In the present example, a case where the objective measurement data is selected will be described as an example.

For example, when the operation unit 83 is operated by the examiner and the objective measurement data is selected, the controller 81 outputs an instruction signal for setting the objective measurement data as the initial value to the information processor 20 (specifically, the controller 21). For example, the controller 21 receives the instruction signal from the controller 81. For example, when receiving the instruction signal, the controller 21 sets the acquired objective measurement data as the initial value of the calibration optical system 11. With such a configuration, for example, it is possible to provide the data to the remote information processor that remote-accesses the information processor of the subjective optometry device that requires the data corresponding to the identifier. In this way, even when operating the subjective optometry device from the remote access destination (for example, a remote location or the like), the examiner can confirm the examinee data, and thus, it is possible to set an appropriate initial value of the subjective optometry device on which the initial setting should be performed.

In the configuration described above, as the subjective optometry system in a case of using the remote information processor, the configuration having a plurality of subjective optometry devices is described as an example, but the present disclosure is not limited to this. As the subjective optometry system in a case of using the remote information processor may be a case of having at least one or more subjective optometry devices.

What is claimed is:

1. A subjective optometry system comprising:
a plurality of subjective optometry devices, which are used to subjectively measure optical characteristics of a subject eye, each including:
a calibration optical system that changes optical characteristics of a target light flux presented to the subject eye;
an information processor for operating the subjective optometry device; and
a reader that is connected to the information processor, reads an identifier prepared for each examinee, and outputs information about the read identifier to the information processor; and
a database that stores at least any data of objective measurement data and previous glass data in association with each identifier,
wherein the information processor is configured to:
acquire at least one of the objective measurement data and the previous glass data corresponding to the identifier from the database, based on the identifier received from the reader; and
set an initial value of the calibration optical system used on an occasion of subjectively measuring optical characteristics of the subject eye, based on at least one of the objective measurement data and the previous glass data.

2. The subjective optometry system according to claim 1, wherein when the information processor receives information of the identifier, the information processor is configured to automatically acquire at least one of the objective measurement data and the previous glass data corresponding to the identifier from the database, and automatically set the initial value of the calibration optical system based on at least one of the objective measurement data and the previous glass data.

3. The subjective optometry system according to claim 1, further comprising:
a data acquisition device configured to acquire at least one of the objective measurement data and the previous glass data; and
a database setting device configured to record at least one of the objective measurement data and the previous glass data acquired by the data acquisition device, in the database, in association with the identifier.

4. The subjective optometry system according to claim 1, wherein subjective measurement data measured at different date and time is further stored in the database in association with each identifier, and
the information processor is configured to:
acquire the subjective measurement data from the database based on the identifier received from the reader; and set the initial value of the calibration optical system used on an occasion of subjectively measuring the optical characteristics of the subject eye based on the subjective measurement data.

5. The subjective optometry system according to claim 1, wherein each of the plurality of subjective optometry devices includes a memory, and any memory out of the plurality of subjective optometry devices is used as the database.

6. The subjective optometry system according to claim 1, wherein each of the plurality of subjective optometry devices includes a memory, and the subjective optometry system further comprises:
    a selection unit configured to selectively set a memory used as the database among a dedicated memory which is different from the memory and is dedicated to set the database, and the memories of the subjective optometry devices.

7. The subjective optometry system according to claim 5, further comprising:
    a relay unit that is connected to the subjective optometry device and the information processor, relays an operation signal from the information processor to the subjective optometry device, and allows the subjective optometry device to be operated based on the operation signal,
    wherein the relay unit is also used as the memory.

8. The subjective optometry system according to claim 1, further comprising:
    a remote information processor that is connected to the information processor, and remote-accesses the information processor to operate at least any subjective optometry device among the plurality of subjective optometry devices via the information processor,
    wherein the information processor outputs acquired data being at least one of the objective measurement data and the previous glass data to the remote information processor to notify the remote information processor of at least one of the objective measurement data and the previous glass data.

9. The subjective optometry system according to claim 8, wherein the remote information processor outputs an instruction signal for setting the initial value of the calibration optical system used on an occasion of subjectively measuring the optical characteristics of the subject eye, and the information processor sets the initial value of the calibration optical system which is based on at least one of the objective measurement data and the previous glass data, according to the instruction signal from the remote information processor.

10. A subjective optometry system comprising:
a subjective optometry device, which is used to subjectively measure optical characteristics of a subject eye, including:
    a calibration optical system that changes optical characteristics of a target light flux presented to the subject eye;
    an information processor for operating the subjective optometry device; and
    a reader that is connected to the information processor, reads an identifier prepared for each examinee, and outputs information about the read identifier to the information processor;
a database that stores at least any data of objective measurement data and previous glass data in association with each identifier; and
a remote information processor that is connected to the information processor, and remote-accesses the information processor to operate the subjective optometry device via the information processor,
wherein the information processor is configured to:
    acquire at least one of the objective measurement data and the previous glass data corresponding to the identifier from the database, based on the identifier received from the reader; and
    output acquired data being at least one of the objective measurement data and the previous glass data to the remote information processor to notify the remote information processor of at least one of the objective measurement data and the previous glass data.

11. The subjective optometry system according to claim 10,
wherein the remote information processor outputs an instruction signal for setting an initial value of the calibration optical system used on an occasion of subjectively measuring the optical characteristics of the subject eye, and
the information processor sets the initial value of the calibration optical system which is based on at least one of the objective measurement data and the previous glass data, according to the instruction signal from the remote information processor.

* * * * *